(12) United States Patent
Bristow

(10) Patent No.: US 9,840,455 B2
(45) Date of Patent: Dec. 12, 2017

(54) PROCESS FOR PURIFYING METHYL ACETATE MIXTURES

(71) Applicant: BP CHEMICALS LIMITED, Middlesex (GB)

(72) Inventor: Timothy Crispin Bristow, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 15/311,965

(22) PCT Filed: Jun. 12, 2015

(86) PCT No.: PCT/EP2015/063147
§ 371 (c)(1),
(2) Date: Nov. 17, 2016

(87) PCT Pub. No.: WO2015/193182
PCT Pub. Date: Dec. 23, 2015

(65) Prior Publication Data
US 2017/0081271 A1    Mar. 23, 2017

(30) Foreign Application Priority Data

Jun. 20, 2014  (EP) .................................. 14173354

(51) Int. Cl.

| | | |
|---|---|---|
| *C07C 41/16* | (2006.01) | |
| *C07C 43/04* | (2006.01) | |
| *C07C 51/09* | (2006.01) | |
| *C07C 53/08* | (2006.01) | |
| *C07C 67/37* | (2006.01) | |
| *C07C 67/54* | (2006.01) | |
| *C07C 69/14* | (2006.01) | |
| *C07C 41/42* | (2006.01) | |
| *B01D 3/14* | (2006.01) | |
| *B01D 3/42* | (2006.01) | |

(52) U.S. Cl.
CPC .............. *C07C 67/54* (2013.01); *B01D 3/143* (2013.01); *B01D 3/4205* (2013.01); *C07C 41/16* (2013.01); *C07C 41/42* (2013.01); *C07C 51/09* (2013.01); *C07C 67/37* (2013.01)

(58) Field of Classification Search
CPC ........ C07C 67/54; C07C 51/09; C07C 43/043
See application file for complete search history.

(56) References Cited

U.S. PATENT DOCUMENTS 3,337,620 A * 8/1967 Binning et al. .......... B01D 3/40
                                                      203/42
7,465,822 B2    12/2008  Cheung et al.

FOREIGN PATENT DOCUMENTS

| WO | WO 2011/027105 A1 |   | 3/2011 |
| WO | WO 2011027105 A1 | * | 3/2011 |
| WO | WO 2013/124404 A1 |   | 8/2013 |
| WO | WO 2013/124423 A1 |   | 8/2013 |

* cited by examiner

*Primary Examiner* — Paul A Zucker
(74) *Attorney, Agent, or Firm* — Nixon & Vanderhye P.C.

(57) ABSTRACT

A process for removing acetaldehyde from a mixture of methyl acetate, dimethyl ether and acetaldehyde comprising distilling mixtures derived from carbonylating dimethyl ether in the presence of a zeolite catalyst to generate an overhead stream depleted in acetaldehyde as compared to the feed mixture, a base stream depleted in acetaldehyde as compared to the feed mixture and a sidedraw stream enriched in acetaldehyde as compared to the feed mixture and withdrawing from the column the sidedraw stream enriched in acetaldehyde at a point above the feed point of the feed mixture to the column. Purified mixtures may be utilized as feedstock to processes for the co-production of acetic acid and dimethyl ether.

19 Claims, 3 Drawing Sheets

PROCESS FOR PURIFYING METHYL ACETATE MIXTURES

This application is the U.S. national phase of International Application No. PCT/EP2015/063147 filed Jun. 12, 2015 which designated the U.S. and claims priority to European Patent Application No. 14173354.3 filed Jun. 20, 2014, the entire contents of each of which are hereby incorporated by reference.

The present invention relates to a process for removing acetaldehyde from mixtures of methyl acetate, acetaldehyde and dimethyl ether. The purified methyl acetate is useful as a feedstock for processes for the co-production of acetic acid and dimethyl ether.

Co-production processes for the manufacture of acetic acid and dimethyl utilise methyl acetate and methanol as feedstocks to the process. Lower alkyl esters such as methyl acetate may be produced by carbonylating alkyl ethers, for example dimethyl ether, with carbon monoxide-containing feeds in the presence of zeolite catalysts. Such carbonylation processes are described in, for example U.S. Pat. No. 7,465,822.

WO 2011027105 describes processes for the co-production of acetic acid and dimethyl ether which utilise acid zeolites to catalyse the dehydration and hydrolysis of feedstock mixtures of methanol and methyl acetate.

WO 2013124404 describes processes for the co-production of acetic acid and dimethyl ether from mixtures of methanol and methyl acetate by contacting a mixture at a temperature of 200 to 260° C. with a catalyst composition comprising a zeolite having a 2-dimensional channel system which comprises at least one channel having a 10-membered ring and a silica:alumina molar ratio of at least 22:1.

WO 2013124423 describes processes for the co-production of acetic acid and dimethyl ether from mixtures of methanol and methyl acetate by contacting a mixture with a zeolite catalyst having a 2-dimensional channel system which comprises at least one channel having a 10-membered ring and at least 5% of its cation exchange capacity occupied by one or more alkali metal cations.

It has now been found that crude reaction products from carbonylation processes and, in particular crude reaction products from processes for carbonylating dimethyl ether with a carbon monoxide-containing gas in the presence of a zeolite catalyst may contain acetaldehyde. However, the presence of significant levels of acetaldehyde in feed streams to processes for the co-production of acetic acid and dimethyl ether is undesirable as acetaldehyde has been found to have a deleterious effect on the catalytic performance of solid acid catalysts, and in particular solid Brønsted acid catalysts, utilised in such processes.

Thus, there remains a need for the provision of purified feedstocks, and in particular the provision of purified methyl acetate feedstocks, which can be directly utilised in processes for the manufacture of acetic acid and dimethyl from methyl acetate and methanol feedstocks conducted in the presence of a catalyst, and in particular in the presence of solid acid catalysts such as solid Brønsted acid catalysts.

Accordingly, the present invention provides a process for removing acetaldehyde from a mixture of methyl acetate, dimethyl ether and acetaldehyde comprising
(i) feeding a mixture of methyl acetate and acetaldehyde and dimethyl ether to a distillation column;
(ii) distilling the mixture to generate an overhead stream depleted in acetaldehyde as compared to the feed mixture, a base stream depleted in acetaldehyde as compared to the feed mixture and a sidedraw stream enriched in acetaldehyde as compared to the feed mixture;
(iii) withdrawing from the column the sidedraw stream enriched in acetaldehyde at a point above the feed point of the feed mixture to the column wherein the feed mixture to the distillation column is derived from one or more processes for carbonylating dimethyl ether with carbon monoxide in the presence of a zeolite carbonylation catalyst.

In the process of the present invention, removal of acetaldehyde from a feed mixture of methyl acetate, acetaldehyde and dimethyl ether is implemented by a fractional distillation method in a distillation column. Acetaldehyde is removed as a volatile component as a sidedraw above the feed point of the feed mixture to the column, dimethyl ether is removed as a light component from the head of the column and methyl acetate is removed as a heavy component from the base of the column.

If so desired, the distilled dimethyl ether may be directly utilised as a feed to processes for carbonylating dimethyl ether with a carbon monoxide-containing gas to generate methyl acetate without the need for further purification and/or be used as a feedstock to other chemical processes.

Advantageously, the purified methyl acetate can be directly fed to a process for the co-production of acetic acid and dimethyl ether without the need for further purification.

Thus the present invention further provides a process for the co-production of acetic acid and dimethyl ether comprising:
(a) purifying a mixture of methyl acetate, acetaldehyde and dimethyl ether by:
   (i) feeding the mixture of methyl acetate, acetaldehyde and dimethyl ether to a distillation column;
   (ii) distilling the feed mixture to generate an overhead stream depleted in acetaldehyde as compared to the feed mixture, a base stream depleted in acetaldehyde as compared to the feed mixture and comprising methyl acetate and a sidedraw stream enriched in acetaldehyde as compared to the feed mixture;
   (iii) withdrawing from the column the sidedraw stream enriched in acetaldehyde at a point above the feed point of the feed mixture to the column.
(b) feeding at least part of the base stream together with optional methanol to a reaction zone containing at least one catalyst effective to produce a crude reaction product comprising acetic acid and dimethyl ether;
(c) recovering acetic acid and dimethyl ether from the crude reaction product.

Figure 1:
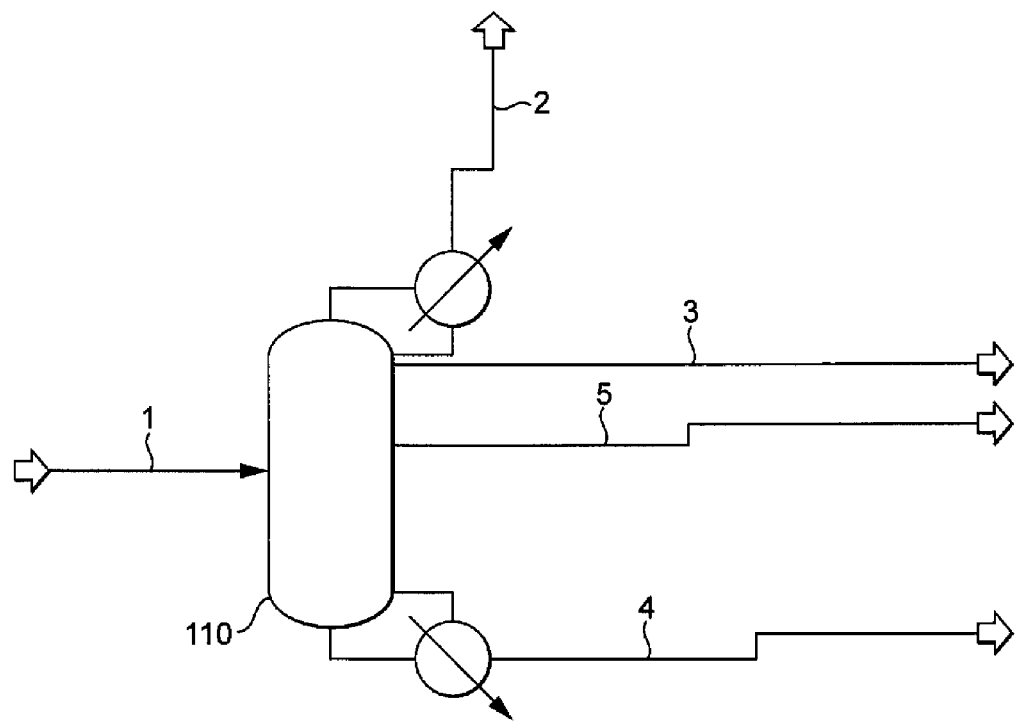
FIG. 1 is a schematic diagram illustrating an embodiment of the present invention for the purification in a single distillation step of a feed mixture comprising methyl acetate, dimethyl ether and acetaldehyde to remove acetaldehyde therefrom.

Acetaldehyde may be present in the feed mixture to the column in an amount >100 ppm up to 1 mol %, such as more than 100 ppm, more than 200 ppm or more than 500 ppm or more than 1000 ppm or more than 2000 ppm or up to 1 mol % acetaldehyde.

In one or more embodiments of the present invention, in step (i) the feed mixture to the column contains methyl acetate, acetaldehyde and >0 to 50 mol % dimethyl ether, such as 5 to 45 mol %, for example 10 to 40 mol %, for instance 10 to 30 mol % dimethyl ether.

In one or more embodiments of the present invention, in step (i) a feed mixture of methyl acetate, acetaldehyde and dimethyl ether comprises >0 to 50 mol % dimethyl ether and up to 1 mol %, for example >100 ppm to 1 mol % acetaldehyde.

In step (i) the feed mixture may be derived from one or more processes for carbonylating dimethyl ether with carbon monoxide in the presence of a zeolite carbonylation catalyst, for example one or both of mordenite and ferrierite zeolite catalysts, and optionally hydrogen to produce methyl acetate. Such feed mixture generally comprise, as principal components, methyl acetate and dimethyl ether together with impurity levels of acetaldehyde. In such cases, the feed mixture to the distillation column might have an acetaldehyde content of >100 ppm up to 1 mol %, such as 100 ppm or more, or 200 ppm or more, or 500 ppm or more or 1000 ppm or more, or 2000 ppm or more or up to 1 mol % acetaldehyde. The feed mixture may further comprise one or more of small amounts of acetic acid, water and dissolved gases such as one or more of carbon oxides and hydrogen and methane. Thus, in addition to acetaldehyde, a feed mixture might comprise 50 to 80 mol % methyl acetate, >0 to 30 mol %, for example 10 to 20 mol % dimethyl ether, 0 to 3 mol % acetic acid, 0 to 20 mol % water and 0 to 10 mol % of one or more of carbon oxides and hydrogen.

Suitably, in step (ii) the distillation column is operated at elevated pressure, such as at a pressure of about 0.5 barg (50 kPa) or more, such as from about 0.5 barg to 30 barg (50 to 3000 kPa), for example from about 10 to 30 barg (1000 to 3000 kPa).

In one or more embodiments of the present invention, in step (ii) the distillation column is operated at a pressure of from 10 to 30 barg (1000 to 3000 kPa) and at a heads temperature of 40 to 90° C.

In step (ii) the distillation column may be operated with a return of liquid reflux to the head of the column at a reflux to heads ratio dependent upon such factors as the desired heads stream composition. At operating pressures of from 10 to 30 barg (1000 to 3000 kPa) and a heads temperature of 40 to 90° C., a suitable reflux ratio is in the range 1 to 4, for example 1.5 to 2.5. Suitably, a boil-up ratio may be in the range 2 to 8.

Suitably, the distillation column has at least 5, such as at least 15 theoretical stages, for example 20 to 60 theoretical stages. Since distillation columns may have differing efficiencies 15 theoretical stages may be equivalent to at least 25 actual stages with an efficiency of about 0.7 or at least 30 actual stages with an efficiency of about 0.5.

In step (i) a feed mixture may be fed to the distillation column as a vapour or as a liquid. Desirably, a feed mixture is fed to the column as a liquid. The heads stream depleted in acetaldehyde and comprising mainly dimethyl ether may be withdrawn as a vapour. Typically, a heads stream might comprise at least 60 mol % dimethyl ether, for example 60 to 95 mol % dimethyl ether. At least a portion of the heads vapour may be condensed and a portion of the condensed liquid returned to the column as reflux.

In step (iii) a sidedraw stream enriched in acetaldehyde as compared to the feed mixture is withdrawn from the distillation column at a point above the feed point of the feed mixture to the column. Recovery of acetaldehyde in the sidedraw stream can be enhanced by providing sufficient stripping capacity in the distillation column below the feed point of the feed mixture to the column. Thus, it is preferred that the distillation column has at least 3 theoretical stages, for example 3 to 10 theoretical stages, below the feed point of the feed mixture.

To optimise recovery of acetaldehyde in the sidedraw stream, it is preferred that in step (iii) the sidedraw stream is withdrawn from the column at or near the point of maximum concentration of acetaldehyde within the column. As would be recognised by the skilled person in the art, the point in the column at which the concentration of acetaldehyde will be at its highest is dependent upon the specific operating conditions employed and, in particular the specific pressure, temperature and reflux ratio employed. Concentrations of components within the column can readily be determined, for example by compositional analysis of distillation mixtures at varying stages of the column, such as compositional analysis by gas chromatographic techniques.

Typically, for a 40 stage column, the feed point of the feed mixture to the column may be at stages 10 to 25 counted from the head of the column and the sidedraw stream withdrawn at stages 4 to 15 counted from the head, provided that the sidedraw is withdrawn from the column at a stage above the feed stage of the column.

In one or more embodiments of the present invention, the distillation column of step (i) is a 40 stage column operated at a pressure of 10 to 30 barg, a heads temperature of 40 to 90° C. and a reflux ratio of from 1 to 4, the feed point of the feed mixture to the column may be at stages 10 to 25 counted from the head of the column and the sidedraw stream withdrawn at stages 4 to 15 counted from the head.

Preferably, in step (iii) the sidedraw stream is withdrawn from the distillation column as a liquid. In addition to acetaldehyde, the sidedraw stream may further comprise amounts of one or both of dimethyl ether and methyl acetate Distillation of the feed mixture generates a base stream depleted in acetaldehyde as compared to the feed mixture. The base stream comprises methyl acetate and preferably comprises the majority of methyl acetate present in the feed mixture to the column. The base stream may also comprise a small proportion of the acetaldehyde present in the feed mixture, such as 100 ppm or less acetaldehyde.

In various embodiments of the present invention, the process is effective to provide an acetaldehyde content in the base stream of 100 ppm or less, 75 ppm or less or 50 ppm or less where the feed mixture has an acetaldehyde content of more than 100 ppm or more than or more than 200 ppm or more than 500 ppm or more than 1000 ppm or more than 2000 ppm.

In step (i) the feed mixture may comprise >0 to 80 mol % methyl acetate, for example 50 to 80 mol %, more than 100 ppm acetaldehyde or more than 500 ppm acetaldehyde or more than 1000 ppm acetaldehyde or more than 2000 ppm acetaldehyde up to 1 mol % acetaldehyde and >0 to 50 mol % dimethyl ether, for example 10 to 30 mol %. In such cases, the process of the present invention is effective to provide a base stream having an acetaldehyde content of about 0 to 100 ppm.

Advantageously, the base stream or a part thereof depleted in acetaldehyde and comprising methyl acetate may be supplied directly to a process for the co-production of acetic acid and dimethyl ether by dehydration-hydrolysis in the presence of a catalyst without the need for further purification.

Thus, in one or more embodiments of the present invention, the base stream or a part thereof comprising methyl acetate is utilised as a feedstock in a process for the co-production of acetic acid and dimethyl ether by the hydrolysis of methyl acetate and dehydration of methanol in the presence of at least one catalyst, for example at least one solid acid catalyst, for example at least one solid Brønsted acid catalyst.

Processes of the present invention for the co-production of acetic acid and dimethyl ether require a source of methyl acetate and a source of methanol. Methanol feedstock for such processes may be synthesised by the catalytic conversion of gaseous mixtures of carbon monoxide, hydrogen and carbon dioxide. Generally, the crude reaction product of these methanol synthesis processes comprises methanol, dimethyl ether, water and, as a result of side-reactions, small quantities of methyl formate.

The presence of methyl formate in process streams for use in processes for the co-production of acetic acid and dimethyl ether from methanol and methyl acetate is undesirable as it can lead to the generation of formic acid. Formic acid is difficult to separate from acetic acid product by conventional fractional distillation techniques owing to the closeness of their boiling points. Instead more complex extractive distillation methods are employed to achieve acetic acid product purities. Complex methods of this type for the separation of formic acid from acetic acid are described in, for example U.S. Pat. No. 4,692,219 and U.S. Pat. No. 5,227,029.

Advantageously, it has now been found that mixtures of dimethyl ether, methyl acetate and acetaldehyde can be distilled in accordance with the process of the present invention together with mixtures comprising methyl formate, such as mixtures of dimethyl ether, methanol, water, and methyl formate. In such cases, methyl formate is removed as a volatile component of the sidedraw stream from the distillation column, dimethyl ether is removed as a lights component from the head of the column and methanol is removed as a heavy component from the base of the column.

Suitably, a feed mixture of dimethyl ether, methanol, water and methyl formate comprises dimethyl ether, methanol and water as principal components and methyl formate as an impurity. The feed mixture may also comprise small quantities of other components such as one or more of carbon oxides, hydrogen, acetaldehyde and methyl acetate.

Thus, in one or more embodiments of the present invention, in step (i) there is further introduced into the distillation column a feed mixture of dimethyl ether, methanol, water and methyl formate, for example in which the methyl formate content is 100 ppm or more or 500 ppm or more. Preferably, the majority of the methyl formate present in the feed is removed as a component of the sidedraw stream.

A mixture of dimethyl ether, methanol, water and methyl formate may be supplied to the distillation column as a combined feed with a mixture of methyl acetate, acetaldehyde and dimethyl ether or as a separate feed to the column.

In one or more embodiments of the present invention, a mixture of dimethyl ether, methanol, water and methyl formate, suitably comprising >0 to 1000 ppm methyl formate, such as 100 ppm or more or 500 ppm or more methyl formate is derived from one or more processes selected from processes for the production of dimethyl ether from methanol by dehydration, suitably by dehydration of methanol in the presence of a zeolite catalyst and processes for the production of methanol by the catalytic conversion of one or more carbon oxides and hydrogen.

A feed mixture of dimethyl ether, methanol, water and methyl formate might comprise >0 to 60 mol %, for example 10 to 40 mol % methanol, >0 to 60 mol %, for example 5 to 40 mol % water, and the balance dimethyl ether, for example 40 to 90 mol % dimethyl ether and methyl formate, for example more than 100 ppm or more than 500 ppm methyl formate.

In one or more embodiments of the present invention, the feed mixture to the distillation column comprises methyl acetate, dimethyl ether and acetaldehyde, suitably in an amount of up to 1 mol %, for example >100 ppm to 1 mol % acetaldehyde, and is distilled together with a feed mixture of dimethyl ether, methanol, water and methyl formate, suitably in an amount of >0 to 1000 ppm methyl formate, such as 100 ppm or more or 500 ppm or more methyl formate.

In one or more embodiments of the present invention, in step (i) there is introduced into the distillation column a combined feed mixture of dimethyl ether, methyl acetate, methanol, water, acetaldehyde and methyl formate. The combined feed mixture may also comprise small quantities of other components such as one or more of carbon oxides, hydrogen, acetic acid and formic acid. Preferably, a combined feed mixture fed to the distillation column comprises acetaldehyde in an amount up to 1 mol % and up to 1000 ppm mol methyl formate.

If, in step (i) a feed mixture of dimethyl ether, methanol, water and methyl formate is introduced to the distillation column as a separate feed, it is preferably fed to the column at a point below the point at which the sidedraw stream is withdrawn from the column. Typically, for a 40 stage column the feed point of the feed mixture of dimethyl ether, methanol, water and methyl formate to the column may be at stages 10 to 25 counted from the head of the column and the sidedraw stream withdrawn at stages 4 to 15 counted from the head provided that the sidedraw is withdrawn at a point above the feed point to the column.

A feed mixture of dimethyl ether, methanol, water and methyl formate may be fed to the column as a liquid and/or as a vapour.

Methanol, as a heavy component in the distillation, is removed from the column together with methyl acetate as part of the base stream. Typically, the base stream will comprise the majority of the water present in the feeds) to the column. Thus, the base stream comprising methyl acetate may further comprise methanol and water and suitably has an acetaldehyde content of not more than 100 ppm.

The process of the present invention is effective to purify a combined feed mixture of dimethyl ether, methanol, water, methyl acetate, acetaldehyde and methyl formate such that the base stream from the distillation column has a methyl formate content of 0 to 100 ppm in cases where the feed mixture to the column has a total methyl formate content of 100 ppm or more, or 500 ppm or more.

In one or more embodiments of the present invention, the base stream from the distillation column has a methyl formate content of 0 to 100 ppm where a feed mixture of dimethyl ether, methanol, water and methyl formate has a methyl formate content of 100 ppm or more, or 500 ppm or more and also an acetaldehyde content of 0 to 100 ppm, for example 100 ppm or less or 75 ppm or less or 50 ppm or less where the feed mixture of dimethyl ether, methyl acetate and acetaldehyde has an acetaldehyde content of more than 100 ppm.

Typically, in step (iii), the sidedraw stream withdrawn from the distillation column and enriched in acetaldehyde also comprises one or more of the feed components to the column. Thus, the sidedraw stream may further comprise one or more of methyl acetate and dimethyl ether. In cases where one or more of (i) additional feed streams, such as return (recycle) streams comprising methyl formate or (ii) feed streams comprising a mixture of dimethyl ether, methanol, water and methyl formate are also fed to the distillation column, the majority of methyl formate introduced into the column is also removed as a component of the sidedraw stream. In such cases, methanol, dimethyl ether and water may also be components of the sidedraw stream.

Dimethyl ether, methanol and methyl acetate are valuable as feedstock components to the processes of the present invention and to other chemical processes. It is therefore desirable to recover these components from mixtures thereof and to further eliminate acetaldehyde and methyl formate components from the process.

Thus, the present invention yet further provides an additional step (iv) in which at least a portion of the sidedraw stream withdrawn from the distillation column in step (iii) comprises acetaldehyde, dimethyl ether and one or more of methyl acetate, methanol and water and is supplied as feed to a second distillation column and is distilled therein to withdraw from the column a sidedraw stream enriched in acetaldehyde as compared to the feed mixture, a heads stream comprising dimethyl ether and a base stream comprising one or more of methyl acetate, methanol and water.

In step (iv) acetaldehyde is removed as a volatile component as a sidedraw stream from the distillation column, dimethyl ether is removed as a light component from the head of the column and methyl acetate, methanol and water are removed as heavy components from the base of the column.

In preferred embodiments of step (iv), the sidedraw stream withdrawn from the distillation column in step (iii) further comprises methyl formate and is supplied as feed to the second distillation column. In this embodiment, methyl formate is removed as a component of the sidedraw stream from the second distillation column.

In preferred embodiments of step (iv) the sidedraw stream withdrawn from the second distillation column comprises the majority of acetaldehyde present in the feed to the column and more preferably, if present in the feed to the second column, the majority of the methyl formate. Desirably, 90% or more, such as 95% or more acetaldehyde and, if present, 90% or more, such as 95% or more methyl formate are removed as components of the sidedraw stream withdrawn from the second distillation column.

A typical configuration of a distillation column for use in step (iv) has up to 40 theoretical stages. Suitably, the distillation column may have 20 to 35 theoretical separation stages and the feed to the column may be introduced at stages 5 to 25 counted from the head of the column and a sidedraw stream withdrawn from the column at stages 5 to 25 counted from the head.

In step (iv) it is not necessary to withdraw the sidedraw stream from above the feed point to the second distillation column, the sidedraw stream may be withdrawn from the column at any desired point but it is desirable that the sidedraw stream is withdrawn from the column at or near the point of maximum concentration of acetaldehyde or if present, methyl formate, within the column. In this manner the majority of the acetaldehyde and, if present the majority of methyl formate, fed to the column and at the greatest concentration thereof can be removed from the column.

Preferably, in step (iv) the sidedraw stream is withdrawn from the second distillation column as a vapour.

If desired, in step (iv) the sidedraw stream withdrawn from the distillation column may be discarded from the process, for example by burning.

In one or more embodiments of the present invention, in step (iv) the feed to the second distillation column may comprise 0 to 30 mol %, for example 5 to 20 mol %, methanol, 0 to 30 mol %, for example 5 to 20 mol % water, 0 to 30 mol %, for example 5 to 20 mol % methyl acetate, 0 to 1 mol % or more, such as 1 to 2 mol % methyl formate and 2 mol % or more, such as 2 to 3 mol % acetaldehyde and the balance dimethyl ether. In such cases, distillation is effective to provide a sidedraw stream comprising acetaldehyde and methyl formate in a total concentration of 20 to 40 mol % and which sidedraw stream contains at least 90%, for example at least 95% of acetaldehyde and methyl formate present in the feed to the second distillation column.

Suitably, in step (iv) the second distillation column is operated at elevated pressure, such as at a pressure of about 0.5 barg (50 kPa) or more, such as about 0.5 barg to 30 barg (50 to 3000 kPa), for example about 10 to 30 barg (1000 to 3000 kPa).

To reduce equipment complexity and cost of the process, it is desirable in step (iv) to operate the second distillation column at a slightly lower pressure or at the same pressure as the pressure of the distillation column of step (i). Desirably, in step (iv) the second distillation column is operated at 0.1 to 1 barg lower pressure than the distillation column of step (i).

In one or more embodiments of the present invention, in step (iv) the second distillation column is operated at a pressure of from 10 to 30 barg (1000 to 3000 kPa) and at a heads temperature of about 40 to 90° C.

Preferably, in step (iv) the feed to the second distillation column, that is the sidedraw removed from the distillation column in step (iii), is fed to the second distillation column as a liquid.

Typically, as a light component, the majority of the dimethyl ether present in the feed to the second distillation column is removed as a heads stream from the column. The heads stream may be removed as a liquid or vapour, preferably as a liquid.

Conveniently, dimethyl ether withdrawn as a heads stream from the second distillation column may be condensed and may be fed as a liquid return stream or as part of a return stream to the distillation column in step (i), suitably at or below the feed point to the column of the feed mixture to the column, and preferably below the point at which the sidedraw stream is withdrawn from the column.

Suitably, in step (iv) the second distillation column may be operated at a reflux ratio of 1 to 4 and a boil-up ratio of 2 to 8.

Typically, as a heavy components, the majority of methyl acetate, and if present in the feed to the second distillation column methanol and water are removed as components of the base stream from the column. Typically, the base stream is removed from the second distillation column as a liquid.

Conveniently, in step (iv) the base stream or a portion thereof from the second distillation column comprising one or more of methyl acetate, methanol and water may be fed as a liquid return stream or as part of a return stream to the distillation column in step (i), suitably at or below the feed point to the column of the feed mixture, and preferably below the point at which the sidedraw stream is withdrawn from the column.

Suitably, at least a portion of the base stream from the second distillation column and at least a portion of liquid dimethyl ether may be fed as a single combined return stream to the distillation column of step (i).

Thus, in preferred embodiments of the present invention, one or more streams or at least a portion thereof, withdrawn in step (iv) from the second distillation column are utilised as feed(s) to the distillation column of step (i). Suitably, such a return feed stream may be the heads stream or a part thereof. The one or more streams may comprise one or more components selected from dimethyl ether, methanol, water and methyl acetate.

Advantageously, embodiments of the present invention provide a means of simultaneously reducing undesirable methyl formate and acetaldehyde compounds from feedstocks to acetic acid and dimethyl ether co-production processes to acceptable levels for use therein. As a result of reduced levels of methyl formate, the amount of formic acid introduced into or generated in the co-production process is reduced. As a result of reduced acetaldehyde levels, its deleterious effect on performance of catalysts employed in the process, and in particular on the catalytic performance of solid acid catalysts such as Brønsted acid catalysts, is eliminated or at least mitigated.

The co-production process acetic acid and dimethyl ether of the present invention comprises the steps:
(a) purifying a mixture of methyl acetate, acetaldehyde and dimethyl ether by:
 (i) feeding the mixture of methyl acetate, acetaldehyde and dimethyl ether to a distillation column;
 (ii) distilling the feed mixture to generate a heads stream depleted in acetaldehyde as compared to the feed mixture, a base stream depleted in acetaldehyde as compared to the feed mixture and comprising methyl acetate and a sidedraw stream enriched in acetaldehyde as compared to the feed mixture;
 (iii) withdrawing from the column the sidedraw stream enriched in acetaldehyde at a point above the feed point of the feed mixture to the column.
(b) feeding at least part of the base stream together with optional methanol to a reaction zone containing at least one catalyst effective to produce a crude reaction product comprising acetic acid and dimethyl ether;
(c) recovering acetic acid and dimethyl ether from the crude reaction product.

The base stream from the distillation column or a part thereof comprises methyl acetate and optionally may further comprise one or both of methanol and water. At least part of the base stream is fed to a reaction zone containing at least one catalyst effective to generate from the methyl acetate and methanol feed(s) a crude reaction product comprising acetic acid and dimethyl ether.

Methanol may be a component of the base stream from the distillation column. In cases where methanol is not a component of the base stream, in step (b) methanol is fed to the reaction zone.

Depending on the exact composition of the base stream it may be desirable in step (b) to supply to the reaction zone one or more components selected from methanol, methyl acetate and water. If desired one or more of these components may be fed to the reaction zone as one or more separate feeds.

Step (b) of the co-production process employs at least one catalyst effective to generate from methyl acetate and methanol reactants a crude reaction product comprising acetic acid and dimethyl ether. Acetic acid is produced by the hydrolysis of methyl acetate. Dimethyl ether is produced by the dehydration of methanol.

The hydrolysis of methyl acetate to produce acetic acid and dehydration of methanol to produce dimethyl ether can be represented by equations (1) and (2) respectively:

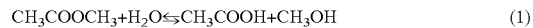

$$CH_3COOCH_3 + H_2O \leftrightharpoons CH_3COOH + CH_3OH \quad (1)$$

$$2CH_3OH \leftrightharpoons CH_3OCH_3 + H_2O \quad (2)$$

The dehydration reaction generates water in-situ and this may be utilised in the hydrolysis reaction. Preferably, however, additional water is fed to the reaction zone. Suitably, water may be fed in an amount of from 0.1 to 50 mol % based on the total feed of methyl acetate, methanol and water to the reaction zone.

The molar ratio of methanol to methyl acetate useful for the dehydration-hydrolysis reaction may be any desired ratio, but suitably the molar ratio of methanol:methyl acetate is in the range 1:0.1 to 1:20.

At least one catalyst is utilised to catalyse the dehydration and hydrolysis reactions. Any suitable catalyst or catalysts may be used provided that it/they are effective to catalyse the hydrolysis of methyl acetate to produce acetic acid and are also effective to catalyse the dehydration of methanol to form dimethyl ether. One or more catalysts may be employed which are effective to catalyse both the hydrolysis and dehydration reactions.

Alternatively, one or more catalysts effective for catalysing the hydrolysis may be used in addition to or as an admixture with one or more catalysts for the dehydration reaction. Where it is desired to employ two or more different catalysts, such catalysts may be utilised in the form of alternating catalyst beds or as one or more intimately mixed catalyst beds.

Preferably, one or more solid acid catalysts are utilised such as one or more solid Brønsted acid catalysts. By 'Brønsted acid catalyst' is meant an acid catalyst which has the ability to donate an acidic proton to facilitate a chemical reaction. Solid acid catalysts useful for the dehydration of methanol include aluminas such as gamma-alumina and fluorinated alumina, acidic zirconias, aluminium phosphate, silica-alumina supported tungsten oxides and solid Brønsted acid catalysts such as heteropolyacids and salts thereof and aluminosilicate zeolites.

The term "heteropolyacid" as used herein and throughout this specification is meant to include the free acids. Heteropolyacids for use herein may be used either as free acids or as partial salts. Typically, the heteropolyacid, or the anionic component of its corresponding salt comprises 2 to 18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for example cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well-known anions are named after the original researchers in this field and are known, for example as Keggin, Wells-Dawson and Anderson-Evans-Perloff structures.

Heteropolyacids usually have a high molecular weight, for example in the range from 700-8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be usefully utilised in the present invention include the free acids such as silicotungstic acids, phosphotungstic acids and 12-tungstophosphoric acid ($H_3$ [$PW_{12}O_{40}$].$xH_2O$); 12-molybdophosphoric acid ($H_3$ [$PMo_{12}O_{40}$].$xH_2O$); 12-tungstosilicic acid ($H_4$[$SiW_{12}$ $O_{40}$].$xH_2O$); 12-molybdosilicic acid ($H_4$[$SiMo_{12}O_{40}$]. $xH_2O$ and ammonium salts of heteropolyacids, such as ammonium salts of a phosphotungstic acid or a silicotungstic acid.

Zeolites known to be effective for the hydrolysis of methyl acetate to produce acetic acid include zeolite Y, zeolite A, zeolite X and mordenite. If desired, these zeolites can be usefully employed as a catalyst in step (b) of the co-production process.

Particularly useful zeolite catalysts for use in step (b) include zeolites having a 2-dimensional or a 3-dimensional channel system at least one channel of which has a 10-membered ring. Specific non-limiting examples of such zeolites include zeolites of framework type FER (typified by ferrierite and ZSM-35), MFI (typified by ZSM-5), MFS (typified by ZSM-57), HEU (for example clinoptilolite) and NES (typified by NU-87).

The three-letter codes such as 'FER' refer to the framework structure type of the zeolites using the nomenclature proposed by the International Zeolite Association. Information about structure codes and zeolites is available in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

The zeolite catalysts may be employed in an exchanged form. Exchanged forms of zeolites can be prepared by techniques such as ion-exchange and impregnation. These techniques are well-known in the art and typically involve the exchange of the hydrogen or ammonium cations of a zeolite with metal cations. For example, in the present invention, the zeolite may be in an exchanged form with one or more alkali metal cations for example sodium, lithium, potassium and cesium. Suitable exchanged form zeolites include ferrierite and ZSM-35 exchanged with one or more of sodium, lithium, potassium and cesium.

A zeolite may be used in the form of a composite with any suitable binder material. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas. Suitably, a binder material may be present in the composite in an amount of from 10 to 90 wt % based on the total weight of zeolite and binder material.

Step (b) may be carried out as a heterogeneous vapour phase process or as a liquid phase process. If it is desired to conduct the process as a vapour phase process, it is preferable to volatilise liquid feed(s), for example in a pre-heater prior to contact with the catalyst(s).

Step (b) may be carried out at temperatures of about 100° C. to 350° C. and at atmospheric pressure or pressures greater than atmospheric.

In one or more embodiments, step (b) is conducted as a vapour phase process at a temperature of about 150° C. to 350° C. and at a pressure of atmospheric to 30 barg (atmospheric to 3000 kPa), for example 5 to 20 barg (500 kPa to 2000 kPa). Suitably, in such cases, step (b) is carried out at a gas hourly space velocity (GHSV) in the range 500 to 40,000 $h^{-1}$.

In one or more embodiments, step (b) is conducted as a liquid phase process and at a temperatures of from about 140° C. to about 210° C. and a pressure which is sufficient to maintain dimethyl ether product in solution, such as pressures of 40 barg (4000 kPa) or higher, for example 40 to 100 barg (4000 to 10,000 kPa). Suitably, in such cases, step (b) is carried out at a liquid hourly space velocity (LHSV) in the range 0.2 to 20 $h^{-1}$.

Step (b) may be carried out using any suitable technique and apparatus, for example by reactive distillation. Reactive distillation techniques and apparatus therefor are well-known. The base stream comprising methyl acetate and optionally additional methanol can be supplied to a conventional reactive distillation column, operated at, for example a pressure in the range atmospheric to 20 barg (atmospheric to 2000 kPa) and at a reaction temperature of about 100° C. to 350° C., to produce a crude reaction product comprising a mixture of acetic acid and dimethyl ether, which mixture is inherently separated within the reactive distillation column to recover a product stream rich in dimethyl ether, typically recovered as an overhead from the column, and a product stream rich in acetic acid which is typically recovered as a base stream from the column.

Alternatively, the reaction zone of step (b) may be a fixed bed reactor or a slurry bed reactor.

The crude reaction product of step (b) comprises dimethyl ether and acetic acid. The crude reaction product may further comprise one or more of methyl acetate, methanol, water, acetaldehyde, methyl formate and formic acid.

Depending on the pressure, dimethyl ether has a boiling point of −24° C. and acetic acid has a boiling point of 118° C. Owing to the difference in their boiling points, acetic acid and dimethyl ether may be recovered from the crude reaction product generated in step (b) by conventional purification methods, such as by distillation in one or more conventional distillation columns. Suitable distillation columns include tray or packed columns. The temperatures and pressures employed in the columns can vary. Suitably, a distillation column may be operated at a pressure, for example of atmospheric to 20 barg (0 to 2000 kPa). Typically, a stream rich in dimethyl ether is recovered as an overhead from the distillation column, and a stream rich in acetic acid is recovered as a base stream from the column.

One or both of the recovered dimethyl ether-rich and acetic acid-rich streams may comprise one or more of methanol, methyl acetate and water. These components may be removed from one or both of the dimethyl ether-rich and acetic acid-rich streams by conventional purification processes, such as by distillation in one or more distillation columns and re-utilised as recycle streams to the process.

In one or more embodiments of the present invention, the crude reaction product of step (b) is treated, suitably by a distillation process, in one or more distillation columns, to recover an acetic-rich stream, suitably as a base stream and a dimethyl ether-rich stream comprising dimethyl ether and one or more of acetaldehyde, methyl formate and formic acid, suitably as a heads stream, and at least a part of the dimethyl ether-rich stream is returned as a feed to the distillation column in step (i).

Acetic acid may be sold or may be used as a feedstock in a variety of chemical processes, such as the manufacture of vinyl acetate or ethyl acetate.

Dimethyl ether may be sold or used as a fuel or as a feedstock to carbonylation processes or to other chemical processes.

The co-production process may be operated as a continuous process or as a batch process, preferably operated as a continuous process.

The invention is now illustrated with reference to the following non-limiting Examples.

EXAMPLE 1

Figure 2:
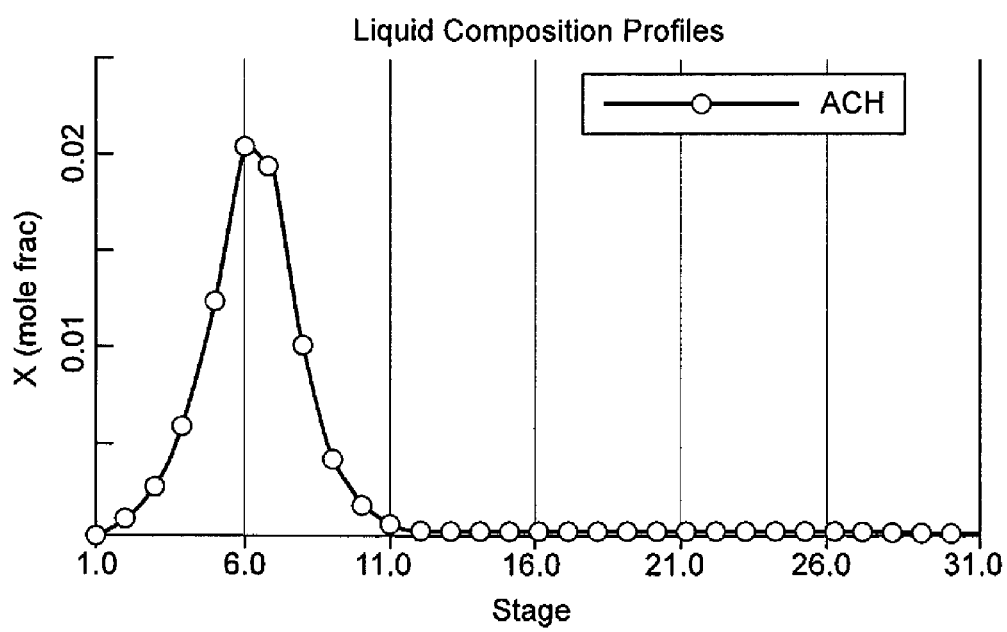
FIG. 2 is a liquid profile composition of acetaldehyde at various stages of a distillation column.

This Example demonstrates in accordance with the present invention, a process for purifying in a single distillation step a mixture comprising methyl acetate, dimethyl ether and acetaldehyde such as may be derived from the carbonylation of dimethyl ether with carbon monoxide in the presence of a catalyst, for example a zeolite catalyst and hydrogen. Reference is made to FIGS. 1 and 2 and Tables 1 to 3. FIG. 1 illustrates schematically a distillation column (110) for carrying out embodiments of the process of the present invention. A feed stream (1) comprising mainly methyl acetate, dimethyl ether and small amounts of acetaldehyde is introduced into distillation column (110) equipped with a reboiler. Distillation column (110) has 30 theoretical stages with the feed point on stage 15 (counted from the head of the column) and is operated at a pressure of 11.7 barg, a heads temperature of 45° C. and a base temperature of 148° C. A heads stream (3) comprising mainly dimethyl ether is removed from the column (110). A vent stream (2) is removed from the column (110), condensed and a portion thereof is returned to the column at a reflux ratio of 2.1 and a boil-up ratio of 0.70. A stream (4) comprising mainly methyl acetate with lesser amounts of water and acetaldehyde is removed as a base stream from the column (110). A sidedraw stream (5) comprising the majority of the acetaldehyde fed to the column (110) is removed from the column on one of stages 3, 6 or 12.

FIG. 2 is a profile of the concentration of acetaldehyde at various stages in the column for the feed composition used in this Example. The profile indicates that in respect of the feed composition used in this Example that the maximum concentration of acetaldehyde occurs at stage 6.

Utilising the procedure and apparatus of the type illustrated in FIG. 1, simulations were carried out using ASPEN software version 7.3. The stream compositions (in units kmol/hr and mol %) are shown in Tables 1 to 3 below. Tables 1 to 3 provides the results for removal of the sidedraw at stage 6; at stage 3 and at stage 12 respectively. In the Tables, the following abbreviations are used:

CO—carbon monoxide
$CO_2$—carbon dioxide
$H_2$—hydrogen
MeOH—methanol
AcOH—acetic acid
DME—dimethyl ether
MeOAc—methyl acetate
AcH—acetaldehyde As can be seen from the results provided in Tables 1 to 3, withdrawing a sidedraw stream at the point of maximum concentration of acetaldehyde within the column (stage 6) results in a much higher amount of acetaldehyde being removed as a component of the sidedraw compared to the amounts removed when a sidedraw is withdrawn from higher and lower stages of the column where the concentration of acetaldehyde is lower.

TABLE 1

| | Stream (mol flow/mol %) | | | | | | | | | |
|---|---|---|---|---|---|---|---|---|---|---|
| | 1 | | 2 | | 3 | | 4 | | 5 | |
| CO | 5.0 | 0.03 | 4.5 | 1.1 | 0.5 | 0.01 | 0.0 | 0.0 | 0.0 | 0.0 |
| $CO_2$ | 194.0 | 1.3 | 67.9 | 16.7 | 126 | 3.5 | 0.0 | 0.0 | 0.3 | 0.3 |
| $H_2$ | 11.0 | 0.1 | 10.2 | 2.5 | 0.8 | 0.02 | 0.0 | 0.0 | 0.0 | 0.0 |
| MeOH | 927.0 | 6.0 | 0.0 | 0.0 | 0.2 | 0.01 | 926.2 | 8.1 | 0.6 | 0.6 |
| AcOH | 108.0 | 0.7 | 0.0 | 0.0 | 0.0 | 0.0 | 108.0 | 0.9 | 0.0 | 0.0 |
| Water | 2208.0 | 14.3 | 0.0 | 0.0 | 0.5 | 0.01 | 2204.2 | 19.4 | 3.2 | 3.2 |
| DME | 3917.0 | 25.3 | 322.3 | 79.6 | 3438.6 | 96.4 | 56.9 | 0.5 | 82.5 | 82.5 |
| MeOAc | 8092.0 | 52.3 | 0.001 | 0.0 | 0.04 | 0.002 | 8080.6 | 71.0 | 11.4 | 11.4 |
| AcH | 5.0 | 0.00 | 0.035 | 0.009 | 1.3 | 0.035 | 1.6 | 0.015 | 2.1 | 2.1 |

TABLE 2

| | Stream (mol flow/mol %) | | | | | | | | | |
|---|---|---|---|---|---|---|---|---|---|---|
| | 1 | | 2 | | 3 | | 4 | | 5 | |
| CO | 5.0 | 0.03 | 4.5 | 1.1 | 0.5 | 0.01 | 0.0 | 0.0 | 0.0 | 0.0 |
| $CO_2$ | 194.0 | 1.3 | 67.9 | 16.8 | 125.7 | 3.5 | 0.0 | 0.0 | 0.4 | 0.4 |
| $H_2$ | 11.0 | 0.1 | 10.2 | 2.5 | 0.8 | 0.02 | 0.0 | 0.0 | 0.0 | 0.0 |
| MeOH | 927.0 | 6.0 | 0.0 | 0.0 | 0.2 | 0.005 | 926.8 | 8.1 | 0.0 | 0.03 |
| AcOH | 108.0 | 0.7 | 0.0 | 0.0 | 0.0 | 0.00 | 108.0 | 0.9 | 0.0 | 0.0 |
| Water | 2208.0 | 14.3 | 0.0 | 0.0 | 0.5 | 0.015 | 2207.3 | 19.4 | 0.2 | 0.15 |
| DME | 3917.0 | 25.3 | 322.6 | 79.6 | 3438.6 | 96.35 | 57.0 | 0.5 | 98.8 | 98.80 |
| MeOAc | 8092.0 | 52.3 | 0.0 | 0.0 | 0.04 | 0.001 | 8091.9 | 71.0 | 0.1 | 0.06 |
| AcH | 5.0 | 0.03 | 0.07 | 0.018 | 2.6 | 0.074 | 1.7 | 0.015 | 0.6 | 0.57 |

TABLE 3

| | Stream (mol flow/mol %) | | | | | | | | | |
|---|---|---|---|---|---|---|---|---|---|---|
| | 1 | | 2 | | 3 | | 4 | | 5 | |
| CO | 5.0 | 0.03 | 4.5 | 1.1 | 0.5 | 0.01 | 0.0 | 0.0 | 0.0 | 0.0 |
| CO$_2$ | 194.0 | 1.3 | 65.7 | 16.7 | 128.1 | 3.5 | 0.0 | 0.0 | 0.2 | 0.2 |
| H$_2$ | 11.0 | 0.1 | 10.1 | 2.6 | 0.9 | 0.024 | 0.0 | 0.0 | 0.0 | 0.0 |
| MeOH | 927.0 | 6.0 | 0.0 | 0.0 | 0.2 | 0.005 | 921.4 | 8.1 | 5.4 | 5.4 |
| AcOH | 108.0 | 0.7 | 0.0 | 0.0 | 0.0 | 0.0 | 108.0 | 1.0 | 0.0 | 0.0 |
| Water | 2208.0 | 14.3 | 0.0 | 0.0 | 0.6 | 0.02 | 2193.2 | 19.4 | 14.2 | 14.2 |
| DME | 3917.0 | 25.3 | 313.8 | 79.6 | 3526.3 | 96.4 | 56.6 | 0.5 | 20.4 | 20.4 |
| MeOAc | 8092.0 | 52.3 | 0.0003 | 0.0001 | 0.04 | 0.001 | 8032.2 | 71.0 | 59.7 | 59.7 |
| AcH | 5.0 | 0.0 | 0.083 | 0.021 | 3.1 | 0.085 | 1.7 | 0.015 | 0.10 | 0.10 |

EXAMPLE 2

This Example demonstrates the effect of acetaldehyde impurities on the catalytic performance of zeolite catalysts in processes for the production of acetic acid and dimethyl ether.

The experiments were carried out in a reactor system capable of carrying out gas phase reactions on solid acid catalysts. The system comprised 64 separate straight tube reactors of internal diameter of approximately 2 mm, capable of holding between 0.01 and 0.1 g of solid catalyst material crushed and sieved to a size fraction between 100 and 200 microns.

The zeolite catalysts tested were alumina extrudates of H-ZSM-5 and H-ferrierite. Prior to use, each of the catalysts were crushed and sieved to a particle size in the range 100-200 microns.

10 mg of a catalyst was placed in a reactor and heated to a temperature of 180° C. for 1 hour under a flow of inert gas (N$_2$/He mixture) at which point, the gas feed to the reactor was changed to provide a reaction feed comprising 20 mol % methanol and methyl acetate at a molar ratio of 1:1 and 80 mol % inert gas. The feed contained 1,1-dimethoxyethane in amounts ranging from 115 to 2100 ppm wt so as to provide total acetaldehyde and 1,1-dimethoxyethane concentrations as shown in Tables 1 and 2 below, calculated as acetaldehyde mass equivalents.

The reaction was allowed to proceed for 96 hours at a temperature of 180° C. and a total pressure of 10 barg and 56 ppm wt 1,1 dimethoxyethane. After 96 hours, the amount of 1,1-dimethoxyethane present in the feed was increased to 703 ppm wt. The reaction was allowed to continue at a temperature of 180° C. and a total pressure of 10 barg for a further 96 hours.

The product stream from a reactor was analysed by gas chromatography to provide composition data for feed and product components. The results of the experiments are shown in Tables 4 and 5 below. In the Tables 'STY' denotes space time yield to a product.

TABLE 4

| Catalyst | Time Period (Hours on Stream) | Mass equivalents of acetaldehyde (ppm wt) | Rate of dimethyl ether STY loss per day (g/kg/hr/day) | Rate of acetic acid STY loss per day (g/kg/hr/day) | Estimated catalyst lifetime to zero production (days) |
|---|---|---|---|---|---|
| H-ZSM-5 | 140-190 | 56 | 8 | 29 | 499 |
| H-ZSM-5 | 140-190 | 703 | 2072 | 360 | 2 |
| H-FER | 140-190 | 56 | 13 | 7 | 312 |
| H-FER | 140-190 | 703 | 61 | 31 | 65 |

TABLE 5

| Catalyst | Time Period (Hours on Stream) | Mass equivalents of acetaldehyde (ppm wt) | Rate of dimethyl ether STY loss per day (g/kg/hr/day) | Rate of acetic acid STY loss per day (g/kg/hr/day) | Estimated catalyst lifetime to zero production (days) |
|---|---|---|---|---|---|
| H-ZSM-5 | 140-225 | 56 | 12 | 28 | 291 |
| H-ZSM-5 | 225-250 | 1034 | 2751 | 478 | 1 |
| H-FER | 140-225 | 56 | 4 | 8 | 806 |
| H-FER | 225-300 | 1034 | 77 | 29 | 45 |

The results given in Tables 4 and 5 clearly demonstrate that the presence of more than a 100 ppm wt acetaldehyde is detrimental to the activity and lifetime of zeolite catalysts.

EXAMPLE 4

Figure 3:
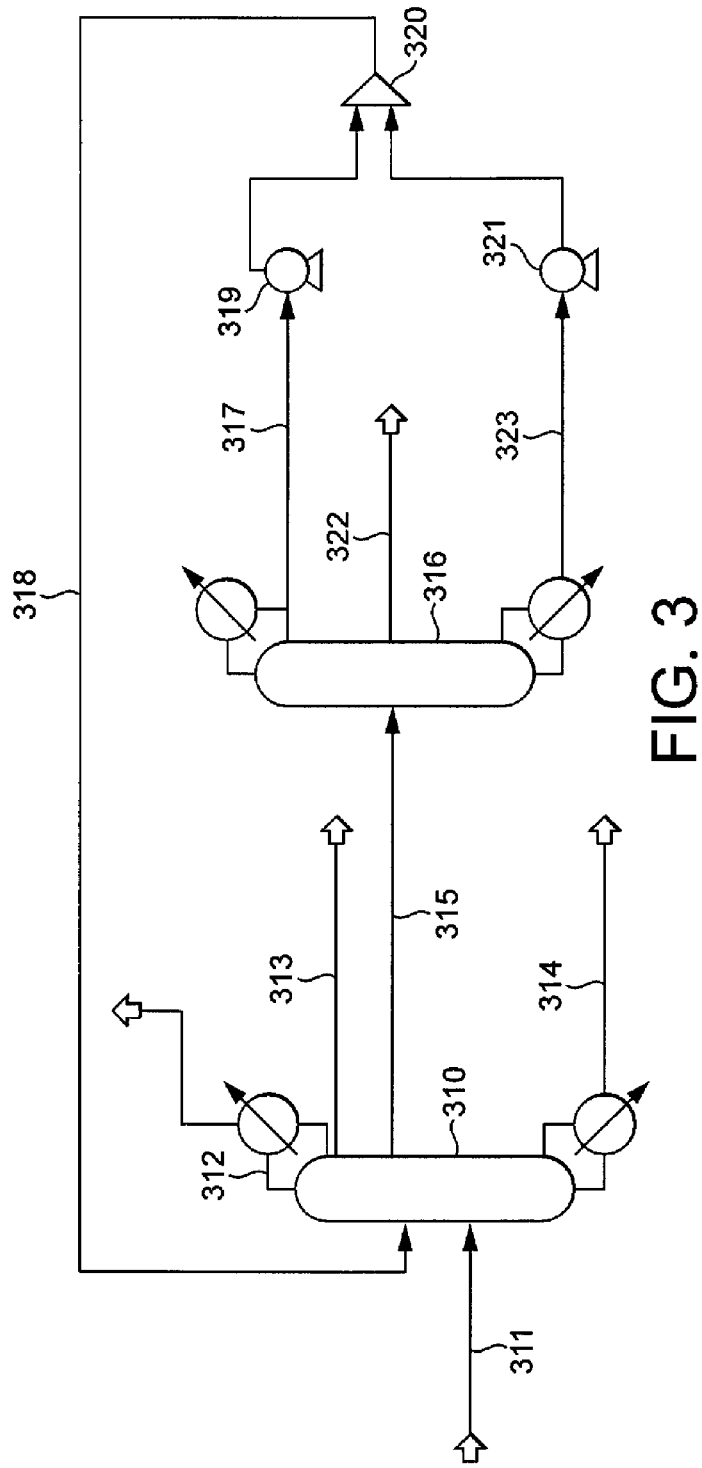
FIG. 3 is a schematic diagram illustrating an embodiment of the present invention for the two-stage purification of a feed mixture comprising methyl acetate, dimethyl ether, acetaldehyde and methyl formate to remove acetaldehyde and methyl formate impurities therefrom.

This Example demonstrates in accordance with the present invention, a two-step process for purifying a mixture comprising methyl acetate, dimethyl ether, methanol, acetaldehyde and methyl formate utilising a two distillation columns. Reference is made to FIG. 3 and Table 6. FIG. 3 illustrates schematically two distillation columns (310) and (316) for carrying out embodiments of the process of the present invention. A feed stream (311) comprising methyl acetate, dimethyl ether and small amounts of acetaldehyde and methyl formate is introduced into distillation column (310) equipped with a reboiler and distilled therein. Distillation column (310) has 30 theoretical stages with the feed point on stage 15 (counted from the head of the column) and is operated at a pressure of 11.7 barg, a heads temperature of 45° C. and a base temperature of 146° C. A vent stream (312) is removed from the column (310), condensed and a portion thereof is returned to the column at a reflux ratio of 3.9 and a boil-up ratio of 0.46. A stream (313) comprising mainly dimethyl ether is withdrawn as a heads stream from the distillation column (310). A stream (314) comprising mainly methyl acetate and depleted in acetaldehyde is removed as a base stream from the column (310). A sidedraw stream (315) comprising dimethyl ether, methyl acetate, water, methanol and the majority of the acetaldehyde and methyl formate fed to the column (310) is removed from stage 6 of column (310) as a liquid.

The sidedraw stream (315) withdrawn from the distillation column (310) is supplied as feed to a second distillation column (316) and distilled therein. Distillation column (316) has 30 theoretical stages with the feed point on stage 10 (counted from the head of the column) and is operated at a pressure of 10.5 barg, a heads temperature of 51° C. and a base temperature of 152° C. A heads stream (317) comprising dimethyl ether is removed from the column (316), condensed and a portion thereof is returned to the column at a reflux ratio of 3.9 and a boil-up ratio of 7.4. The remaining portion of stream (317) is returned to column (310) via pump (319) and compressor (320) as part of recycle stream (318). A stream (323) comprising mainly methyl acetate is removed as a base stream from the column (316) and returned to column (310) via pump (321) and compressor (320) as part of recycle stream (318). A sidedraw stream (322) enriched in acetaldehyde and methyl formate as compared to the feed to column (316) is removed from column (316) on stage 18 of the column (310) as a vapour.

Utilising the procedure and apparatus of the type illustrated in FIG. 3, simulation of the distillation was carried out using ASPEN software version 7.3. The compositions of the various streams (in units kmol/hr and mol %) are shown in Table 6 below. In Table 6, the following abbreviations are used:

CO—carbon monoxide
$CO_2$—carbon dioxide
$H_2$—hydrogen
$CH_4$—methane
MeOH—methanol
AcOH—acetic acid
DME—dimethyl ether
MeOAc—methyl acetate
AcH—acetaldehyde
MeOFO—methyl formate As can be seen from the results shown in Table 6, the process of the present invention is effective to purify feedstreams comprising methyl acetate and methanol and with acetaldehyde and methyl formate as impurities, to acceptable levels of acetaldehyde and methyl format; for subsequent use in processes for the co-production of acetic acid and dimethyl ether from methyl acetate and methanol containing-feedstocks.

TABLE 6

| | Stream mol flow/mol % | | | | | | | | | |
|---|---|---|---|---|---|---|---|---|---|---|
| | 311 | | 312 | | 313 | | 314 | | 315 | |
| CO | 3.00 | 0.04 | 2.76 | 1.96 | 0.24 | 0.02 | 0.00 | 0.00 | 0.00 | 0.00 |
| $CO_2$ | 40.00 | 0.53 | 16.13 | 11.48 | 23.87 | 2.40 | 0.00 | 0.00 | 0.06 | 0.11 |
| $H_2$ | 7.00 | 0.09 | 10.20 | 2.50 | 0.42 | 0.04 | 0.00 | 0.00 | 0.00 | 0.00 |
| $CH_4$ | 3.00 | 0.04 | 2.15 | 1.53 | 0.85 | 0.09 | 0.00 | 0.00 | 0.00 | 0.00 |
| MeOH | 1000.00 | 13.32 | 0.01 | 0.01 | 0.33 | 0.03 | 999.07 | 15.69 | 4.40 | 7.33 |
| AcOH | 69.00 | 0.92 | 0.00 | 0.00 | 0.00 | 0.00 | 69.00 | 1.08 | 0.00 | 0.00 |
| Water | 2000.00 | 26.63 | 0.00 | 0.00 | 0.16 | 0.02 | 1999.00 | 31.39 | 3.46 | 5.76 |
| DME | 1175.00 | 15.65 | 112.75 | 80.30 | 966.71 | 97.29 | 95.54 | 1.50 | 33.40 | 55.66 |
| MeOAc | 3207.00 | 42.71 | 0.00 | 0.00 | 0.03 | 0.00 | 3204.96 | 50.32 | 15.46 | 25.77 |
| AcH | 4.00 | 0.05 | 0.03 | 0.02 | 0.96 | 0.01 | 0.83 | 0.01 | 2.76 | 4.60 |
| MeOFO | 1.00 | 0.01 | 0.00 | 0.00 | 0.06 | 0.01 | 0.53 | 0.01 | 0.46 | 0.76 |

| | Stream (mol flow/mol %) | | | | | | | |
|---|---|---|---|---|---|---|---|---|
| | 317 | | 318 | | 322 | | 323 | |
| CO | 0.00 | 0.00 | 0.00 | 0.00 | 0.00 | 0.00 | 0.00 | 0.00 |
| $CO_2$ | 0.06 | 0.19 | 0.06 | 0.12 | 0.00 | 0.00 | 0.00 | 0.00 |
| $H_2$ | 0.00 | 0.00 | 0.00 | 0.00 | 0.00 | 0.00 | 0.00 | 0.00 |
| $CH_4$ | 0.00 | 0.00 | 0.00 | 0.00 | 0.00 | 0.00 | 0.00 | 0.00 |
| MeOH | 0.00 | 0.00 | 3.82 | 7.07 | 0.58 | 9.70 | 3.82 | 19.19 |
| AcOH | 0.00 | 0.00 | 0.00 | 0.00 | 0.00 | 0.00 | 0.00 | 0.00 |
| Water | 0.01 | 0.02 | 2.62 | 4.86 | 0.83 | 13.88 | 2.62 | 13.16 |
| DME | 33.39 | 97.90 | 33.39 | 61.84 | 0.00 | 0.00 | 0.00 | 0.00 |
| MeOAc | 0.00 | 0.00 | 13.45 | 24.92 | 2.01 | 33.48 | 13.45 | 67.65 |
| AcH | 0.58 | 1.71 | 0.59 | 1.08 | 2.18 | 36.27 | 0.00 | 0.00 |
| MeOFO | 0.06 | 0.17 | 0.06 | 0.11 | 0.40 | 6.66 | 0.00 | 0.00 |

EXAMPLE 5

Figure 4:
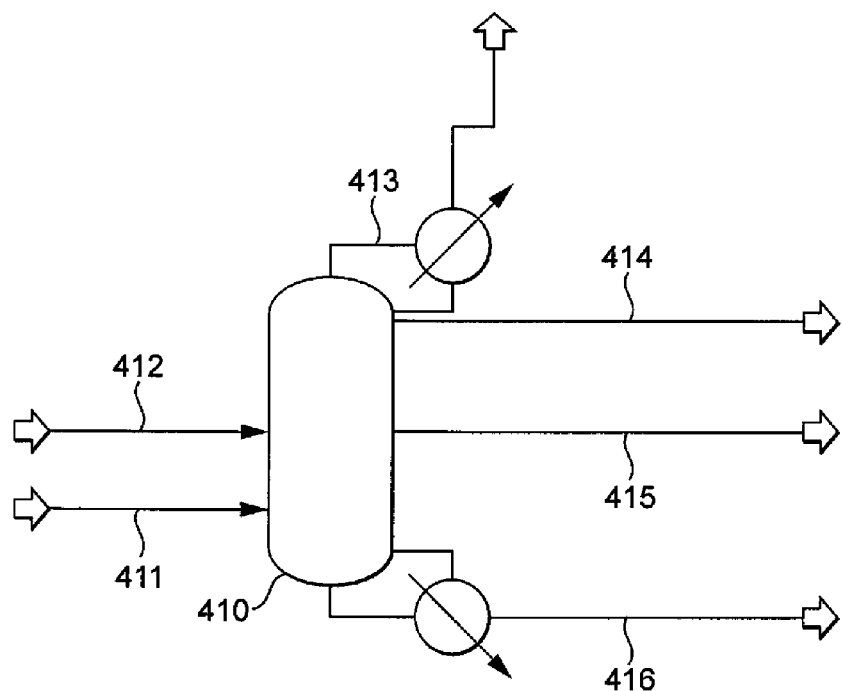
FIG. 4 is a schematic diagram illustrating an embodiment of the present invention for the purification in a single distillation step of a combined feed mixture comprising methyl acetate, dimethyl ether, methanol, water, acetaldehyde and methyl formate to remove acetaldehyde and methyl formate impurities therefrom.

This Example demonstrates in accordance with the present invention, a process for purifying in a single distillation step a combined feed mixture comprising methyl acetate, dimethyl ether, water, methanol, acetaldehyde and methyl formate. Reference is made to FIG. 4 and Table 7. FIG. 4 illustrates schematically a distillation column (410) for carrying out embodiments of the process of the present invention. Distillation column (410) is equipped with a reboiler and is supplied with a first feedstream (411) comprising methyl acetate, dimethyl ether and small amounts of acetaldehyde and a second feedstream (412) comprising dimethyl ether, methanol, water and methyl formate as a contaminant and the first and second feedstreams are distilled together therein. Distillation column (410) has 30 theoretical stages with the feed point for feedstream (411) on stage 24 and for feedstream (412) on stage 11 (counted from the head of the column) and is operated at a pressure of 11.7 barg, a heads temperature of 45° C. and a base temperature of 147° C. A vent stream (413) is removed from the column (410), condensed and a portion of the condensed stream is returned to the column at a reflux ratio of 3.7 and a boil-up ratio of 0.92. A stream (414) comprising principally dimethyl ether is withdrawn as a heads stream from the distillation column (410). A stream (416) comprising mainly methyl acetate, methanol and water and depleted in acetaldehyde and also methyl formate is removed as a base stream from column (410). A sidedraw stream (415) comprising dimethyl ether and the majority of the acetaldehyde and methyl formate fed to column (410) is removed from stage 6 of column (410) as a liquid.

Utilising the procedure and apparatus of the type illustrated in FIG. 4, simulation of the distillation was carried out using ASPEN software version 7.3. The compositions (in units kmol/hr and mol %) of the various streams are shown in Table 7 below. In Table 7, the following abbreviations are used:
CO—carbon monoxide
$CO_2$—carbon dioxide
$H_2$—hydrogen
MeOH—methanol
AcOH—acetic acid
DME—dimethyl ether
MeOAc—methyl acetate
AcH—acetaldehyde
MeOFO—methyl formate As can be seen from the results shown in Table 7, the process of the present invention is effective to purify in a single distillation step combined feed mixtures of methyl acetate, methanol, water, dimethyl ether and having acetaldehyde and methyl formate present as contaminants therein, to acceptable levels of acetaldehyde and methyl formate, for subsequent use in processes for the co-production of acetic acid and dimethyl ether from methyl acetate and methanol containing-feedstocks.

TABLE 7

| | Stream mol flow/mol % | | | | | | | | | | | |
|---|---|---|---|---|---|---|---|---|---|---|---|---|
| | 411 | | 412 | | 413 | | 414 | | 415 | | 416 | |
| CO | 0.00 | 0.00 | 3.00 | 0.14 | 1.27 | 5.89 | 1.73 | 0.07 | 0.00 | 0.00 | 0.00 | 0.00 |
| $CO_2$ | 0.00 | 0.00 | 17.00 | 0.78 | 0.69 | 3.21 | 16.29 | 0.67 | 0.02 | 0.03 | 0.00 | 0.00 |
| $H_2$ | 0.00 | 0.00 | 4.00 | 0.18 | 2.00 | 9.29 | 2.00 | 0.08 | 0.00 | 0.00 | 0.00 | 0.00 |
| MeOH | 286.00 | 3.97 | 320.00 | 14.59 | 0.00 | 0.01 | 1.10 | 0.05 | 4.67 | 7.79 | 600.23 | 8.73 |
| AcOH | 36.00 | 0.50 | 0.00 | 0.00 | 0.00 | 0.00 | 0.00 | 0.00 | 0.00 | 0.00 | 36.00 | 0.52 |
| Water | 670.00 | 9.30 | 735.00 | 33.52 | 0.00 | 0.00 | 0.12 | 0.00 | 1.30 | 2.16 | 1403.58 | 20.41 |
| DME | 1404.00 | 19.48 | 1113.00 | 50.75 | 17.58 | 81.57 | 2419.48 | 99.06 | 45.56 | 75.93 | 34.39 | 0.50 |
| MeOAc | 4807.00 | 66.69 | 0.00 | 0.00 | 0.00 | 0.00 | 0.01 | 0.00 | 4.73 | 7.88 | 4802.26 | 69.83 |
| AcH | 5.00 | 0.07 | 0.00 | 0.00 | 0.00 | 0.02 | 1.50 | 0.06 | 2.91 | 4.85 | 0.59 | 0.009 |
| MeOFO | 0.00 | 0.00 | 1.00 | 0.05 | 0.00 | 0.00 | 0.18 | 0.01 | 0.82 | 1.36 | 0.00 | 0.00 |

The invention claimed is:

1. A process for removing acetaldehyde from a mixture of methyl acetate, dimethyl ether and acetaldehyde comprising
(i) feeding a mixture of methyl acetate and acetaldehyde and dimethyl ether to a distillation column;
(ii) distilling the mixture to generate an overhead stream depleted in acetaldehyde as compared to the feed mixture, a base stream depleted in acetaldehyde as compared to the feed mixture and a sidedraw stream enriched in acetaldehyde as compared to the feed mixture;
(iii) withdrawing from the column the sidedraw stream enriched in acetaldehyde at a point above the feed point of the feed mixture to the column; and
wherein the feed mixture to the distillation column is derived from one or more processes for carbonylating dimethyl ether with carbon monoxide in the presence of a zeolite carbonylation catalyst.

2. A process according to claim 1 which comprises a further step (iv) wherein at least a portion of the sidedraw stream withdrawn from the distillation in step (iii) comprises acetaldehyde, dimethyl ether and one or more of methyl acetate, methanol and water and is supplied as feed to a second distillation column and is distilled therein to withdraw from the column a sidedraw stream enriched in acetaldehyde as compared to the feed mixture, a heads stream comprising dimethyl ether and a base stream comprising one or more of methyl acetate, methanol and water.

3. A process according to claim 1 wherein in step (i) the feed mixture comprises methyl acetate, acetaldehyde and >0 to 50 mol % dimethyl ether.

4. A process according to claim 1 wherein in step (i) the feed mixture comprises >100 ppm up to 1 mol % acetaldehyde.

5. A process according to claim 1 wherein in step (i) the feed mixture further comprises one or more of acetic acid, water, carbon oxides and hydrogen.

6. A process according to claim 1 wherein in step (ii) the distillation column is operated at a pressure of 10 barg to 30 barg (1000 to 3000 kPa) and at a heads temperature of 40 to 90° C.

7. A process according to claim 6 wherein the distillation column is operated with a return of liquid reflux to the head of the column at a reflux to heads ratio in the range 1 to 4.

8. A process according to claim 1 wherein the distillation column of step (i) has at least 3 theoretical stages below the feed point of the feed mixture to the column.

9. A process according to claim 1 wherein in step (iii) the sidedraw stream is withdrawn from the column at or near the point of maximum concentration of acetaldehyde.

10. A process according to claim 1 wherein in step (iii) the sidedraw stream is withdrawn from the distillation column as a liquid.

11. A process according to claim 1 wherein in step (ii) the base stream comprises 100 ppm or less of acetaldehyde.

12. A process according to claim 1 wherein in step (i) there is further introduced into the distillation column a mixture of dimethyl ether, methanol, water and methyl formate and wherein the majority of the methyl formate present in the feed is removed as a component of the sidedraw stream.

13. A process according to claim 1 wherein the base stream of step (ii) or a part thereof comprising methyl acetate is utilised as a feedstock in a process for the co-production of acetic acid and dimethyl ether by the hydrolysis of methyl acetate and dehydration of methanol and in the presence of at least one catalyst.

14. A process for the co-production of acetic acid and dimethyl ether comprising:
 (a) purifying a mixture of methyl acetate, acetaldehyde and dimethyl ether by:
 (i) feeding the mixture of methyl acetate, acetaldehyde and dimethyl ether to a distillation column;
 (ii) distilling the feed mixture to generate an overhead stream depleted in acetaldehyde as compared to the feed mixture, a base stream depleted in acetaldehyde as compared to the feed mixture and comprising methyl acetate and a sidedraw stream enriched in acetaldehyde as compared to the feed mixture;
 (iii) withdrawing from the column the sidedraw stream enriched in acetaldehyde at a point above the feed point of the feed mixture to the column;
 (b) feeding at least part of the base stream together with optional methanol to a reaction zone containing at least one catalyst effective to produce a crude reaction product comprising acetic acid and dimethyl ether;
 (c) recovering acetic acid and dimethyl ether from the crude reaction product.

15. A process according to claim 14 which comprises a further step (iv) wherein at least a portion of the sidedraw stream withdrawn from the distillation in step (iii) comprises acetaldehyde, dimethyl ether and one or more of methyl acetate, methanol and water and is supplied as feed to a second distillation column and is distilled therein to withdraw from the column a sidedraw stream enriched in acetaldehyde as compared to the feed mixture, a heads stream comprising dimethyl ether and a base stream comprising one or more of methyl acetate, methanol and water.

16. A process according to claim 14 wherein in step (i) the feed mixture is derived from one or more processes for carbonylating dimethyl ether with carbon monoxide in the presence of a zeolite carbonylation catalyst.

17. A process according to claim 14 wherein in step (b) the at least one catalyst is a solid Brønsted acid catalyst.

18. A process according to claim 14 wherein the crude reaction product of step (b) is treated to recover an acetic-rich stream and a dimethyl ether-rich stream comprising dimethyl ether and one or more of acetaldehyde, methyl formate and formic acid, and at least a part of the dimethyl ether-rich stream is returned as a feed to the distillation column in step (i).

19. A process according to claim 14 wherein in step (b) there is supplied to the reaction zone one or more components selected from methanol, methyl acetate and water.

* * * * *